United States Patent
Al Khunaizi et al.

(10) Patent No.: US 11,857,953 B1
(45) Date of Patent: Jan. 2, 2024

(54) METHODS OF MAKING BORONATED ZEOLITES AND PROCESSES FOR CRACKING BUTENE-CONTAINING STREAMS

(71) Applicant: Saudi Arabian Oil Company, Dhahran (SA)

(72) Inventors: Hashim N. Al Khunaizi, Qatif (SA); Ahmad A. Jazzar, Riyadh (SA); Shatha A. Alabbad, Dammam (SA); Donya A. Sewdan, Dammam (SA); Qasim Saleem, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/051,280

(22) Filed: Oct. 31, 2022

(51) Int. Cl.
| | |
|---|---|
| *C01B 39/12* | (2006.01) |
| *B01J 29/40* | (2006.01) |
| *B01J 37/08* | (2006.01) |
| *B01J 37/00* | (2006.01) |
| *C10G 11/05* | (2006.01) |
| *C01B 39/06* | (2006.01) |
| *C01B 39/38* | (2006.01) |
| *B01J 29/86* | (2006.01) |
| *C01B 39/02* | (2006.01) |
| *B01J 37/06* | (2006.01) |

(52) U.S. Cl.
CPC ............ *B01J 29/40* (2013.01); *B01J 29/86* (2013.01); *B01J 37/0045* (2013.01); *B01J 37/06* (2013.01); *B01J 37/08* (2013.01); *C01B 39/02* (2013.01); *C01B 39/06* (2013.01); *C01B 39/12* (2013.01); *C01B 39/38* (2013.01); *C10G 11/05* (2013.01); *B01J 2229/16* (2013.01); *B01J 2229/37* (2013.01); *B01J 2229/38* (2013.01); *B01J 2229/40* (2013.01); *C10G 2400/20* (2013.01)

(58) Field of Classification Search
CPC .. C10G 11/05; C10G 2400/20; B01J 37/0045; B01J 37/08; B01J 37/06; B01J 29/86; B01J 29/40; B01J 2229/40; B01J 2229/37; B01J 2229/38; B01J 2229/16; B01J 2229/183; C01B 39/02; C01B 39/06; C01B 39/12; C01B 39/38

USPC ............................... 423/713, 714; 502/60, 77
See application file for complete search history.

(56) References Cited

U.S. PATENT DOCUMENTS

| | | | |
|---|---|---|---|
| 4,029,716 A | 6/1977 | Kaeding | |
| 4,049,573 A | 9/1977 | Kaeding | |
| 4,140,726 A | 2/1979 | Unland et al. | |
| 4,661,467 A | 4/1987 | Kuehl | |
| 5,981,418 A | 11/1999 | Drake et al. | |
| 6,114,551 A * | 9/2000 | Levin | C07D 301/19 549/510 |
| 6,156,689 A | 12/2000 | Kimble et al. | |
| 6,486,373 B1 | 11/2002 | Abichandani et al. | |

OTHER PUBLICATIONS

Chen et al., "Toluene alkylation over ZSM-5 zeolite catalysts with skeletal and nonskeletal boron", Zeolites, vol. 12, pp. 347-350, Apr./May 1992.
Fild et al., "Cation-induced transformation of born-coordination in zeolites"Phys. Chem. Chem. Phys., vol. 2, pp. 3091-3098, 2000.
Sulikowski et al., "Hydrothermal Isomorphous Substitution of Boron in Zeolite ZSM-5/Silicate", American Chemical Society, Chapter 27, 12 pages, 1989.

\* cited by examiner

*Primary Examiner* — Elizabeth D Wood
(74) *Attorney, Agent, or Firm* — DINSMORE & SHOHL LLP

(57) ABSTRACT

A method of making a boronated zeolite catalyst includes preparing an initial slurry comprising water, a shape selective zeolite, boric acid, and a weak acid selected from the group consisting of oxalic acid, citric acid, and oxalic acid and citric acid, hydrothermally treating the initial slurry at a temperature of from 70° C. to 90° C. to produce a hydrothermally treated slurry comprising dealuminated zeolite particles, adjusting the pH of the hydrothermally treated slurry to an intermediate pH of from 8 to 9 to produce a basic slurry, after adjusting the pH to the intermediate pH, hydrothermally treating the basic slurry at a temperature of from 70° C. to 90° C. to produce a boronated zeolite slurry, removing liquids from the boronated zeolite slurry to produce a boronated zeolite filtrate, and drying and calcining the boronated zeolite filtrate to produce the boronated zeolite catalyst.

12 Claims, 2 Drawing Sheets

METHODS OF MAKING BORONATED ZEOLITES AND PROCESSES FOR CRACKING BUTENE-CONTAINING STREAMS

BACKGROUND

Field

The present disclosure relates to methods of forming catalysts and processes for cracking hydrocarbon feeds to produce light olefins.

Technical Background

The worldwide increasing demand for light olefins remains a major challenge for many integrated refineries. In particular, the production of some valuable light olefins, such as ethylene and propylene, has attracted increased attention as pure olefin streams are considered the building blocks for polymer synthesis. The production of light olefins depends on several process variables, such as the feed type, operating conditions, and the type of catalyst. Despite the options available for producing a greater yield of ethylene and propylene, intense research activity in this field is still being conducted. For example, light olefins can be produced through thermal cracking (or steam pyrolysis) of hydrocarbon feeds. Light olefins can also be produced through catalytic cracking.

SUMMARY

Accordingly, there is an ongoing need for improved catalysts for catalytic cracking of hydrocarbons. In particular, an ongoing need exists for improved catalysts for catalytically cracking butene-containing streams to produce light olefins, such as ethylene and propene. Dealuminated boronated zeolite catalysts can be used; however, production of these catalysts are limited, at least in part, due to limitations of conventional methods requiring multiple drying and calcination steps to produce the catalysts. Accordingly, there is an ongoing need for methods for preparing boronated catalysts and processes for cracking hydrocarbon feeds to produce olefins with high selectivity and yield of light olefins from hydrocarbon feeds compared to conventional methods for preparing boronated catalysts and conventional processes for cracking hydrocarbon feeds. The methods and processes of the present disclosure include boronated zeolite catalysts. In particular, the methods of the present disclosure include making the boronated zeolite catalyst under mild acidic and basic conditions. The mild conditions can allow for the dealumination of zeolite particles followed by the boronation of the dealuminated zeolite particles, without requiring an additional drying and calcining step after dealumination and before boronation, which can improve the economics of catalyst preparation. Further, processes for cracking a butene-containing stream using the boronated zeolite particles can maintain high light olefin yield and selectivity, which can improve the economics of light olefin production, among other features.

According to at least one aspect of the present disclosure, a method of making a boronated zeolite catalyst can comprise preparing an initial slurry comprising water, a shape selective zeolite, boric acid, and a weak acid selected from the group consisting of oxalic acid, citric acid, and oxalic acid and citric acid, where the initial slurry has an initial pH of from 1 to 5, hydrothermally treating the initial slurry at a temperature of from 70° C. to 90° C. to produce a hydrothermally treated slurry comprising dealuminated zeolite particles, adjusting the pH of the hydrothermally treated slurry to an intermediate pH of from 8 to 9 to produce a basic slurry, after adjusting the pH to the intermediate pH, hydrothermally treating the basic slurry at a temperature of from 70° C. to 90° C. to produce a boronated zeolite slurry, removing liquids from the boronated zeolite slurry to produce a boronated zeolite filtrate, and drying and calcining the boronated zeolite filtrate to produce the boronated zeolite catalyst.

Additional features and advantages of the aspects of the present disclosure will be set forth in the detailed description that follows and, in part, will be readily apparent to a person of ordinary skill in the art from the detailed description or recognized by practicing the aspects of the present disclosure.

BRIEF DESCRIPTION OF THE DRAWING

The following detailed description of the present disclosure may be better understood when read in conjunction with the following drawing in which.

Figure 1:
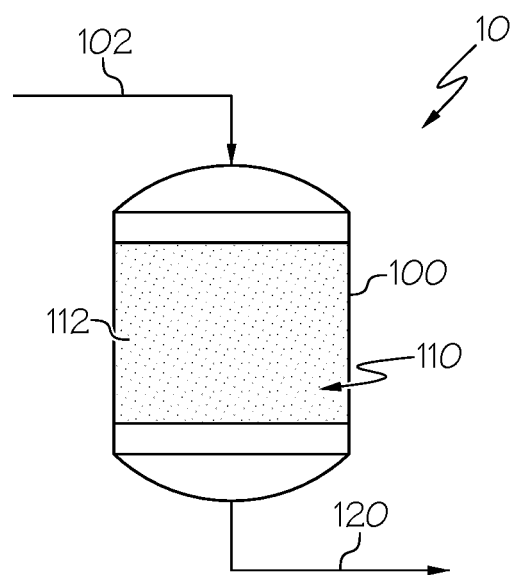
FIG. 1 schematically depicts a generalized flow diagram of a fixed bed reactor system for converting mixed butenes to propylene, ethylene, or both through catalytic cracking, according to one or more embodiments shown and described in the present disclosure.
Figure 2:
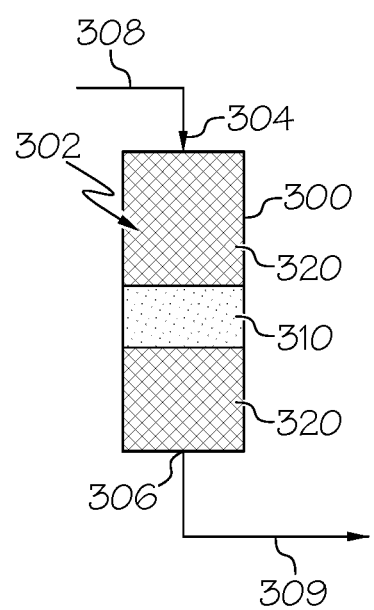
FIG. 2 schematically depicts one reactor compartment of a screening reactor system for evaluating the catalysts of the examples, according to one or more embodiments shown and described in the present disclosure.

When describing the simplified schematic illustrations of FIGS. 1-2, the numerous valves, temperature sensors, electronic controllers, and the like, which may be used and are well known to a person of ordinary skill in the art, may not be included. Further, accompanying components that are often included in systems such as those depicted in FIGS. 1-2, such as air supplies, heat exchangers, surge tanks, and the like also may not be included. However, a person of ordinary skill in the art understands that these components are within the scope of the present disclosure.

Additionally, the arrows in the simplified schematic illustrations of FIGS. 1-2 refer to process streams. However, the arrows may equivalently refer to transfer lines, which may transfer process streams between two or more system components. Arrows that connect to one or more system components signify inlets or outlets in the given system components and arrows that connect to only one system component signify a system outlet stream that exits the depicted system or a system inlet stream that enters the depicted system. The arrow direction generally corresponds with the major direction of movement of the process stream or the process stream contained within the physical transfer line signified by the arrow.

The arrows in the simplified schematic illustration of FIGS. 1-2 may also refer to process steps of transporting a process stream from one system component to another system component. For example, an arrow from a first system component pointing to a second system component may signify "passing" a process stream from the first system component to the second system component, which may comprise the process stream "exiting" or being "removed" from the first system component and "introducing" the process stream to the second system component.

Reference will now be made in greater detail to various aspects, some of which are illustrated in the accompanying drawing.

DETAILED DESCRIPTION

The present disclosure is directed to methods for making boronated zeolite catalysts and processes for cracking butene-containing streams to produce light olefins, such as ethylene and propylene. The methods of making the boronated zeolite catalysts can include preparing an initial slurry comprising water, a shape selective zeolite, boric acid, and a weak acid selected from the group consisting of oxalic acid, citric acid, or oxalic acid and citric acid; hydrothermally treating the initial slurry at a temperature of from 70° C. to 90° C. to produce a hydrothermally treated slurry comprising dealuminated zeolite particles; adjusting the pH of the hydrothermally treated slurry to an intermediate pH of from 8 to 9 to produce a basic slurry; hydrothermally treating the basic slurry at a temperature of from 70° C. to 90° C. to produce a boronated zeolite slurry; removing liquids from the boronated zeolite slurry to produce a boronated zeolite filtrate; washing the boronated zeolite filtrate, and drying and calcining the boronated zeolite filtrate to produce the boronated zeolite catalyst. The processes of the present disclosure for converting mixed butenes to light olefins can include contacting a butene-containing stream with the boronated zeolite catalyst in a reactor, wherein contacting causes at least a portion of the mixed butenes to undergo cracking reactions to form a product stream comprising ethylene and propylene. The methods of making the boronated zeolite catalyst of the present disclosure can enable a one-pot dealuminati on and boronation of zeolite particles, reducing the number of drying and calcination steps required to form the boronated zeolite catalyst. The boronated zeolite catalysts of the present disclosure can enable efficient cracking of butene-containing streams, among other features.

As used in the present disclosure, the term "cracking" refers to a chemical reaction where a molecule having carbon-carbon bonds is broken into more than one molecule by the breaking of one or more of the carbon-carbon bonds. As used in the present disclosure, the term "catalytic cracking" refers to cracking conducted in the presence of a catalyst. Some catalysts may have multiple forms of catalytic activity, and calling a catalyst by one particular function does not render that catalyst incapable of being catalytically active for other functionality.

As used in the present disclosure, the term "catalyst" refers to any substance that increases the rate of a specific chemical reaction, such as cracking reactions.

As used throughout the present disclosure, the terms "butenes" or "mixed butenes" may be used interchangeably and may refer to combinations of one or a plurality of isobutene, 1-butene, trans-2-butene, or cis-2-butene. As used throughout the present disclosure, the term "normal butenes" may refer to a combination of one or a plurality of 1-butene, trans-2-butene, or cis-2-butene. As used throughout the present disclosure, the term "2-butenes" may refer to trans-2-butene, cis-2-butene, or a combinations of these.

As used throughout the present disclosure, the term "C4" may be used to refer to compositions or streams comprising compounds having 4 carbon atoms, the term "C4+" may be used to refer to compositions or streams comprising compounds having 4 or more than 4 carbon atoms, and the term "C5+" may be used to refer to compositions or streams comprising compounds having 5 or more than 5 carbon atoms.

The term "time on-stream" refers to the amount of time that the reaction system is operated with a flow of reactants at reaction conditions. In particular, the "time on-stream" refers to the amount of time that the catalyst, such as the boronated zeolite catalyst, is maintained in contact with the flow of the reactants, such as the butenes in the butene-containing stream, at the reaction conditions, such as at the reaction temperature.

As used in the present disclosure, the term "reactor" refers to any vessel, container, conduit, or the like, in which a chemical reaction, such as catalytic cracking, occurs between one or more reactants optionally in the presence of one or more catalysts. A reactor can include one or a plurality of "reaction zones" disposed within the reactor. The term "reaction zone" refers to a region in a reactor where a particular reaction takes place.

It should be understood that components of a stream are disclosed as passing from one system component to another when a stream comprising that component is disclosed as passing from that system component to another. For example, a disclosed "butene-containing stream" passing to a first system component or from a first system component to a second system component should be understood to equivalently disclose "butenes" passing to the first system component or passing from a first system component to a second system component.

The composition of cracking catalysts used in catalytic cracking play a significant role on reaction yields from catalytic cracking. Boronated zeolite catalysts can be used as cracking catalysts for catalytically cracking hydrocarbons. Conventional methods for producing cracking catalysts comprising boronated zeolites require costly preparation, such as requiring multiple drying and calcination steps. These additional processing steps are energy intensive and increase the economic cost of preparing the cracking catalysts, which increase the cost of producing light olefins, such as ethylene, propylene, or both, from a hydrocarbon feed.

Accordingly, aspects of the present disclosure are directed to methods of making a cracking catalyst comprising a boronated zeolite and processes for cracking butene-containing streams to form product streams comprising ethylene and propylene with the cracking catalyst. The method for preparing the boronated zeolite can include preparing an initial slurry comprising water, a shape selective zeolite, boric acid, and a weak acid; hydrothermally treating the initial slurry to produce a hydrothermally treated slurry comprising dealuminated zeolite particles; adjusting the pH of the hydrothermally treated slurry to an intermediate pH of from 8 to 9 to produce a basic slurry; hydrothermally treating the basic slurry at a temperature of from 70° C. to 90° C. to produce a boronated zeolite slurry; recovering the boronated zeolite; and calcining the boronated zeolite catalysts.

In embodiments, the methods of the present disclosure can include preparing an initial slurry comprising water, a shape selective zeolite, boric acid, and a weak acid selected from the group consisting of oxalic acid, citric acid, and oxalic acid and citric acid. The initial slurry can be prepared by combining the water, boric acid, and the weak acid to form a solution. The shape selective zeolite can then be added to the solution to form the initial slurry. In embodiments, the initial slurry can have a pH of from 1 to 5.

Shape selective zeolites can be active to catalytically crack hydrocarbon compounds, such as mixed butenes or other olefins, to produce one or more lighter olefins, such as ethylene, propylene, or both. Without being bound by any particular theory, it is believed that the shape selective zeolite may have a greater propensity to crack the relatively lighter hydrocarbons, such as mixed butenes and other olefins, compared to other types of zeolites, such as large pore zeolite s. The shape selective zeolite can be an MFI structured zeolite. In embodiments, the shape selective zeolite is ZSM-5 zeolite. As used in the present disclosure, "ZSM-5" refers to zeolites having an MFI framework type according to the IUPAC zeolite nomenclature and consisting of silica and alumina. ZSM-5 refers to "Zeolite Socony Mobil-5" and is a pentasil family zeolite that can be represented by the chemical formula $Na_nAl_nSi_{96-n}O_{192} \cdot 16H_2O$, where $0<n<27$.

In embodiments, the molar ratio of silica to alumina in the shape selective zeolite of the initial slurry can be greater than or equal to 15, greater than or equal to 50, greater than or equal to 100, greater than or equal to 200 or even greater than or equal to 250. In embodiments, the molar ratio of silica to alumina in the shape selective zeolite of the initial slurry can be from 15 to 800, from 15 to 400, from 15 to 300, from 15 to 200, from 15 to 100, from 15 to 50, from 50 to 800, from 50 to 400, from 50 to 300, from 100 to 800, from 100 to 400, from 100 to 300, from 200 to 800, from 200 to 400, from 200 to 300, from 250 to 800, from 250 to 400, or from 250 to 300. Conventional methods of boronating zeolites have been limited to lower silica to alumina ratios, because increasing the silica to alumina molar ratio decreases the proportion of alumina, which makes it difficult to dealuminate the zeolite. The methods of the present disclosure may enable a shape selective zeolite with a greater silica to alumina molar ratio to be used as the starting zeolite compared to conventional methods of boronating zeolites. In particular, the methods of the present disclosure may increase an amount of dealumination of the zeolite and increase an amount of boron deposition, while improving catalytic cracking activity compared to conventional methods of preparing boronated zeolites.

In embodiments, the initial slurry can include less than or equal to 20 wt. % shape selective zeolite based on the total weight of the initial slurry. In embodiments, the initial slurry can include less than or equal to 15 wt. %, or less than or equal to 10 wt. % shape selective zeolite based on the total weight of the initial slurry. In embodiments, the initial slurry can include the shape selective zeolite in an amount of from 5 wt. % to 20 wt. %, from 5 wt. % to 15 wt. %, from 10 wt. % to 20 wt. %, from 10 wt. % to 15 wt. %, or from 12 wt. % to 14 wt. %, based on the total weight of the initial slurry.

In embodiments, the initial slurry can include less than or equal to 1 wt. %, less than or equal to 0.5 wt. %, or less than or equal to 0.1 wt. % boric acid based on the total weight of the initial slurry. In embodiments, the initial slurry can include boric acid in an amount of from 0.01 wt. % to 1 wt. %, from 0.01 wt. % to 0.5 wt. %, from 0.01 wt. % to 0.3 wt. %, from 0.01 wt. % to 0.2 wt. %, or from 0.01 wt. % to 0.1 wt. %, based on the total weight of the initial slurry.

In embodiments, the initial slurry can include a weak acid selected from the group consisting of oxalic acid, citric acid, and oxalic acid and citric acid. In embodiments, the weak acid is oxalic acid. In embodiments, the weak acid is citric acid. In embodiments, the initial slurry can include less than or equal to 1 wt. % of the weak acid based on the total weight of the initial slurry. In embodiments, the initial slurry can include the weak acid in an amount of from 0.01 wt. % to 1 wt. %, from 0.01 wt. % to 0.5 wt. %, from 0.01 wt. % to 0.3 wt. %, or from 0.01 wt. % to 0.2 wt. % based on the total weight of the initial slurry. Without intending to be bound by any particular theory, it is believed that an initial slurry having greater than 1 wt. % of the weak acid may result in greater extent of dealumination of the zeolite, increasing the silica to alumina ratio of the dealuminated zeolite particles to a value greater than desired.

In embodiments, hydrothermally treating the initial slurry can include heating the initial slurry to a temperature of from 70° C. to 90° C. for a duration of time to produce a hydrothermally treated slurry. In embodiments, the initial slurry can be hydrothermally treated for a duration of time from 12 hours to 36 hours. In embodiments, the initial slurry can be hydrothermally treated for about 24 hours. Hydrothermally treating the initial slurry can remove at least a portion of aluminum from the shape selective zeolite. In embodiments, the method can further comprise allowing the hydrothermally treated slurry to return to room temperature after hydrothermally treating the initial slurry. Without intending to be bound by any particular theory, it is believed that the removal of aluminum from the framework can lead to a decrease in the number of sites where framework hydrolysis can occur under hydrothermal and thermal conditions. This removal of aluminum results in an increased thermal and hydrothermal stability in dealuminated zeolites. The unit cell size can decrease as a result of dealumination, since the smaller $SiO_4$ tetrahedron replaces the larger $AlO_4-$ tetrahedron. The acidity of zeolites can also be affected by dealumination through the removal of framework aluminum and the formation of extra-framework aluminum species. Dealumination may affect the acidity of the zeolites by decreasing the total acidity and increasing the acid strength of the zeolite. The total acidity can decrease because of the removal of framework aluminum, which act as Brønsted acid sites. The acid strength of the zeolite may be increased because of the removal of paired acid sites or the removal of the second coordinate next nearest neighbor aluminum. The increase in the acid strength may be caused by the charge density on the proton of the OH group being highest when there is no framework aluminum in the second coordination sphere. In embodiments, the method does not include steaming to dealuminate the zeolite.

In embodiments, the hydrothermally treated slurry, which can comprise at least the dealuminated zeolite, water, and boric acid, may not be actively dried or calcined before adjusting the pH to the intermediate pH. As used in this disclosure, "actively dried" refers to taking an active step, such as but not limited to applying heat, gas flow, or vacuum to the dealuminated zeolite, to increase a rate of mass transfer of solvents, such as water, out of the dealuminated zeolite. Without intending to be bound by any particular theory, it is believed that the lack of actively drying and calcining the hydrothermally treated slurry can reduce the economic cost of preparing the boronated zeolite catalyst.

In embodiments, adjusting the pH of the hydrothermally treated slurry may include adding a base to the hydrothermally treated slurry to adjust the pH to an intermediate pH of from 8 to 9 to produce a basic slurry. In embodiments, the base can include any base capable of adjusting the pH to the intermediate pH of from 8 to 9. The base can be a hydroxide compound, such as but not limited to an alkali metal hydroxide, an alkaline earth metal hydroxide, ammonium hydroxide, or combinations of these. In embodiments, the base can include ammonium hydroxide. Using ammonium hydroxide as the base can reduce or eliminate the presence of alkali or alkaline earth metal ions in the basic slurry, which can reduce the number of steps needed to prepare the boronated zeolite catalyst, increase the yield of the boronated zeolite catalyst, or both compared to using alkali or alkaline earth metal hydroxides. In embodiments, the base may be added stepwise to the hydrothermally treated slurry, and the pH of the hydrothermally treated slurry may be monitored during addition of the base until the pH is from 8 to 9, at which point addition of the base may be ceased.

The methods disclosed herein can include hydrothermally treating the basic slurry at a temperature and for a duration sufficient to deposit boron within the framework and onto the surfaces of the dealuminated zeolite to produce a boronated zeolite. In embodiments, hydrothermally treating the basic slurry may include heating the basic slurry to a temperature of from 70° C. to 90° C. for a duration of time to produce a boronated zeolite slurry comprising the boronated zeolite. In embodiments, the basic slurry can be hydrothermally treated for a duration of time from 12 hours to 36 hours. In embodiments, the basic slurry can be hydrothermally treated for about 24 hours. In embodiments, hydrothermally treating the basic slurry can deposit boron in the dealuminated zeolite to produce the boronated zeolite slurry comprising boronated zeolite. In embodiments, the method can further comprise allowing the boronated zeolite slurry to return to room temperature after hydrothermally treating the basic slurry.

In embodiments, removing liquids from the boronated zeolite slurry may include removing at least a portion of the liquids, such as water, from the boronated zeolite slurry to produce a boronated zeolite filtrate. Processes for removing the liquids from the boronated zeolite can include, but are not limited to filtration, decanting, centrifugation, other solid-liquid separation methods, or combinations of these.

In embodiments, the boronated zeolite filtrate can be washed. The boronated zeolite filtrate can be washed with an aqueous solution, such as water, to remove at least a portion of ionic constituents in the boronated zeolite filtrate. In embodiments, the boronated zeolite filtrate can be washed with deionized water. The boronated zeolite filtrate can be washed with water a plurality of times to remove constituents of the boronated zeolite slurry and other contaminants from the surfaces of the boronated zeolite filtrate. Washing the boronated zeolite filtrate to remove reagents and other contaminants can reduce the pH of the boronated zeolite filtrate closer to neutral pH.

Following washing the boronated zeolite filtrate with an aqueous solution, the methods of the present disclosure can further include removing residual liquids from the boronated zeolite filtrate. The residual liquids can include the water used to wash the boronated zeolite filtrate. In embodiments, removing liquids from the boronated zeolite filtrate can include evaporating the liquids from the boronated zeolite filtrate. In embodiments, the boronated zeolite filtrate can be heated, subjected to reduced pressure such as in a vacuum chamber, or both, to remove the liquids through evaporation. In embodiments, the boronated filtrate can be heated in an oven at an elevated temperature, such as about 90° C., for a duration of time sufficient to produce a solid powder. In embodiments, the drying time may be from 1 hour to 24 hours.

Following drying, the boronated zeolite filtrate can be calcined to produce the boronated zeolite catalyst. In embodiments, calcining the boronated zeolite filtrate can include heating the filtrate to a temperature of from 550° C. to 700° C. for a duration of time sufficient to produce the boronated zeolite catalyst. In embodiments, the time of calcining can include a range of 30 minutes to 10 hours.

In embodiments, the boronated zeolite catalyst can comprise greater than or equal to 3 wt. %, greater than or equal to 5 wt. %, or even greater than or equal to 10 wt. % boron based on the total weight of the boronated zeolite catalyst. In embodiments, the boronated zeolite catalyst can comprise boron in an amount of from 3 wt. % to 15 wt. %, from 3 wt. % to 10 wt. %, from 5 wt. % to 15 wt. %, or from 5 wt. % to 10 wt. % based on the total weight of the boronated zeolite catalyst. Without intending to be bound by any particular theory, it is believed that the inclusion of boron in the boronated zeolite catalyst in an amount of greater than or equal to 3 wt. % may reduce a hydride transfer reaction rate, lowering the aromatization activity of the catalyst, compared to zeolites with less than 3 wt. % boron. Decreasing the aromatization activity can increase yield and selectivity of light olefins, such as ethylene, propene, or both. Without intending to be bound by any particular theory, it is believed that greater than 15 wt. % boron in the boronated zeolite catalyst can significantly decrease the acidity of the catalyst, which can reduce the cracking activity of the catalyst.

In embodiments, the boron can be disposed on the boronated zeolite catalyst in tetrahedral and trigonal planar sites within a framework of the zeolite. In embodiments, the boron can be disposed on the zeolite in trigonal planar extra-framework sites of the boronated zeolite catalyst. Without intending to be bound by any particular theory, it is believed that boron disposed on the zeolite in trigonal planar extra-framework sites can reduce coke formation on the boronated zeolite catalyst and reduce the hydride transfer reaction rate, both of which can increase the cracking activity of the catalyst.

In embodiments, the molar ratio of silica to alumina in the boronated zeolite catalyst, after synthesizing the boronated zeolite catalyst, can be greater than or equal to 20, greater than or equal to 50, greater than or equal to 100, greater than or equal to 200, or even greater than or equal to 250. In embodiments, the molar ratio of silica to alumina in the boronated zeolite catalyst can be from 20 to 1600, from 20 to 800, from 20 to 400, from 20 to 300, from 20 to 200, from 20 to 100, from 20 to 50, from 50 to 1600, from 50 to 800, from 50 to 400, from 50 to 300, from 100 to 1600, from 100 to 800, from 100 to 400, from 100 to 300, from 200 to 1600, from 200 to 800, from 200 to 400, from 200 to 300, from 250 to 1600, from 250 to 800, from 250 to 400, from 250 to 300, from 300 to 1600, from 300 to 800, from 300 to 400, or from 350 to 400. Without intending to be bound by any particular theory, it is believed that a molar ratio of silica to alumina in the boronated zeolite catalyst of less than 20 may not result in an effective pore volume and thus may reduce the activity of the boronated zeolite catalyst in in cracking reactions. It is believed that a molar ratio of silica to alumina in the boronated zeolite catalyst greater than 1600 can cause a reduction in cracking activity due to a reduced number of solid acid sites.

In embodiments, the boronated zeolite catalyst can have an average surface area of greater than or equal to 500 $m^2/g$, or an average surface area of greater than or equal to 525 $m^2/g$. In embodiments, the boronated zeolite catalyst can have an average surface area of from 500 $m^2/g$ to 800 $m^2/g$, from 500 $m^2/g$ to 700 $m^2/g$, or from 500 $m^2/g$ to 600 $m^2/g$. In embodiments, the boronated zeolite catalyst can have an average microporous pore volume of greater than or equal to 0.15 cubic centimeters per gram (cm³/g). In embodiments, the boronated zeolite catalyst can have an average microporous pore volume of from 0.15 cm³/g to 0.600 cm³/g.

In embodiments, the boronated zeolite catalyst can have a crystallinity of greater than or equal to 90%, greater than or equal to 92%, greater than or equal to 94%, or even greater than or equal to 95% of the crystallinity of the initial zeolite material from which the boronated zeolite catalyst may be formed. Greater crystallinity can impart increased stability to the zeolite, especially when exposed to elevated temperatures such as those in catalytic processes. The crystallinity may be measured with XRD (X-ray Diffraction). A commercialized and relatively well-crystallized ZSM-5 zeolite (for example, CBV-2804 from Zeolyst International) may be taken as the reference at 100% crystallinity. From XRD spectra, the five most intensive peaks are integrated. The sample relative crystallinity is calculated based on the following equation: $X(\%)=100\% \times \Sigma A/\Sigma A_0$, where A is the sum of the five peak total area of the fabricated samples; $A_0$ is the sum of the five peak total area of the reference sample (for example, CBV-2804). Without intending to be bound by any particular theory, it is believed that the mild acidic conditions during hydrothermally treating the initial slurry, and/or the mild basic conditions during hydrothermally treating the basic slurry, can produce the highly crystalline boronated zeolite catalyst.

As previously discussed, the boronated zeolite catalyst of the present disclosure can be used in a process for catalytically cracking mixed butenes and other olefins to produce propylene, ethylene, or both. As previously discussed, the process for catalytically cracking olefins to produce propylene, ethylene, or both can include providing a butene-containing stream comprising at least mixed butenes as a feed stream and then contacting the feed stream with the boronated zeolite catalyst of the present disclosure under reaction conditions sufficient to catalytically crack at least a portion of the mixed butenes or other olefins in the feed stream to produce propylene, ethylene, or both.

The feed stream can comprise one or more olefins, such as mixed butenes, mixed pentenes, mixed hexenes, or other olefins. The feed stream can comprise at least mixed butenes, such as but not limited to 1-butene, cis-2-butene, trans-2-butene, isobutene, or combinations of these. In embodiments, the feed stream can be a C4 stream, which can include mixed butenes as well as other C4 compounds, such as but not limited to butane, isobutane, 1,3-butadiene, or combinations of these. In embodiments, the feed stream can be a C4 stream recovered from a steam cracking process, from a fluidized catalytic cracking process, or from both. In embodiments, the feed stream can comprise, consist of, or consist essentially of 1-butene, 2-butenes, isobutane, and n-butane, where the 2-butenes comprise cis-2-butene, trans-2-butene, or both.

In embodiments, the feed stream can comprise 1-butene. In embodiments, the feed stream can comprise from 12.5 wt. % to 50 wt. % 1-butene based on the total mass flow rate of the feed stream. In embodiments, the feed stream can comprise from 12.5 wt. % to 45 wt. %, from 12.5 wt. % to 40 wt. %, from 20 wt. % to 50 wt. %, from 20 wt. % to 45 wt. %, from 20 wt. % to 40 wt. %, from 25 wt. % to 50 wt. %, from 25 wt. % to 45 wt. %, from 25 wt. % to 40 wt. %, from 30 wt. % to 50 wt. %, from 30 wt. % to 45 wt. %, from 30 wt. % to 40 wt. %, or from 40 wt. % to 50 wt. % 1-butene based on the total mass flow rate of the feed stream. In embodiments, the feed stream can comprise 2-butenes, including cis-2-butene, trans-2-butene, or both. In embodiments, the feed stream can comprise from 12.5 wt. % to 30 wt. % 2-butenes based on the total mass flow rate of the feed stream. In embodiments, the feed stream can comprise from 12.5 wt. % to 25 wt. %, from 12.5 wt. % to 20 wt. %, from 12.5 wt. % to 15 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % 2-butenes based on the total mass flow rate of the feed stream.

In embodiments, the feed stream can comprise isobutane. In embodiments, the feed stream can comprise from 15 wt. % to 30 wt. % isobutane based on the total mass flow rate of the feed stream. In embodiments, the feed stream can comprise from 15 wt. % to 25 wt. %, from 15 wt. % to 20 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % isobutane based on the total mass flow rate of the feed stream. In embodiments, the feed stream can comprise n-butane. In embodiments, the feed stream can comprise from 5 wt. % to 55 wt. % n-butane based on the total mass flow rate of the feed stream. In embodiments, the feed stream can comprise from 5 wt. % to 50 wt. %, from 5 wt. % to 45 wt. %, from 5 wt. % to 40 wt. %, from 5 wt. % to 30 wt. %, from 5 wt. % to 10 wt. %, from 10 wt. % to 55 wt. %, from 10 wt. % to 50 wt. %, from 10 wt. % to 45 wt. %, from 10 wt. % to 40 wt. %, from 20 wt. % to 55 wt. %, from 20 wt. % to 50 wt. %, from 20 wt. % to 45 wt. %, from 20 wt. % to 40 wt. %, from 30 wt. % to 55 wt. %, from 30 wt. % to 50 wt. %, from 30 wt. % to 45 wt. %, from 30 wt. % to 40 wt. %, or from 40 wt. % to 55 wt. % n-butane based on the total mass flow rate of the feed stream. The feed stream can also include other C4 constituents, such as but not limited to isobutene, 1,3-butadiene, or other C4 compounds. If present, the 1,3-butadiene concentration in the feed stream can be less than or equal to 0.1 wt. % 1,3-butadiene based on the total mass flow rate of the feed stream.

In embodiments, the feed stream to the catalytic cracking process can be an effluent from a metathesis reactor for converting mixed butenes to propylene, ethylene, or both through one or more metathesis reactions. When the feed stream is an effluent from a metathesis reactor, the feed stream can further include greater molecular weight olefins, such as mixed pentenes, mixed hexenes, or other greater molecular weight olefins resulting from metathesis of mixed butenes. The feed stream can also include propylene, ethylene, or both produced from the metathesis reactions. When the feed stream is an effluent from a metathesis reactor, the feed stream can also include other reaction products resulting from the metathesis reactions.

The feed stream generally does not include nitrogen or air. Without intending to be bound by any particular theory, it is believed that the presence of nitrogen, air, or both can cause side reactions in the cracking reactor resulting in reduced yield of propylene, ethylene, or both. In embodiment, the feed stream is substantially free of nitrogen, air, or both, such as having less than 0.1 wt. % or even less than 0.01 wt. % nitrogen, air, or both based on the total mass flow rate of the feed stream.

Referring now to FIG. 1, a reactor system 10 comprising a cracking reactor 100 for converting the feed stream 102 comprising at least mixed butenes to propylene, ethylene, or both is schematically depicted. The feed stream 102 is passed to the cracking reactor 100, which comprises at least a cracking reaction zone 110 comprising the cracking catalyst 112. In embodiments, the cracking reactor 100 can be a fixed bed reactor. Other types of reactors, such as but not limited to moving bed reactors, fluidized bed reactors, and the like can also be used to for the cracking reactor 100.

Although shown as a downflow reactor in FIG. 1, the cracking reactor 100 can also be an upflow reactor, a horizontal flow reactor, or have any other suitable flow pattern suitable for contacting the feed stream 102 with the cracking catalyst 112.

In the cracking reactor 100, the feed stream 102 comprising the mixed butenes can be contacted with the cracking catalyst 112 at reaction conditions sufficient to cause catalytic cracking of at least a portion of the mixed butenes or other olefins in the feed stream 102 to produce a cracking effluent 120 comprising propylene, ethylene, or both. Contact of the mixed butenes or other olefins in the feed stream 102 with the cracking catalyst 112 at the reaction conditions can cause at least a portion of the mixed butenes or other olefins to undergo cracking reactions to convert the olefins into propylene, ethylene, or both. The feed stream 102 can be contacted with the cracking catalyst 112 in the cracking reaction zone 110 at a temperature sufficient to cause cracking of the olefins to produce the cracking effluent 120 comprising propylene, ethylene, or both. In embodiments, the process can include contacting the feed stream 102 with the cracking catalyst 112 at a temperature of from 300° C. to 650° C., such as from 300° C. to 600° C., from 300° C. to 550° C., from 300° C. to 500° C., from 350° C. to 650° C., from 350° C. to 600° C., from 350° C. to 550° C., from 350° C. to 500° C., from 400° C. to 650° C., from 400° C. to 600° C., from 400° C. to 550° C., from 400° C. to 500° C., from 450° C. to 650° C., from 450° C. to 600° C., from 450° C. to 550° C., from 500° C. to 600° C., or about 550° C. In embodiments, the feed stream 102 can be contacted with the cracking catalyst 112 in the cracking reaction zone 110 at a pressure of from 1 bar (100 kPa) to 30 bar (3,000 kPa) or from 2 bar (200 kPa) to 20 bar (2,000 kPa). In embodiments, the feed stream 102 can be contacted with the cracking catalyst 112 in the cracking reaction zone 110 at atmospheric pressure. In embodiments, the feed stream 102 can be contacted with the cracking catalyst 112 in the cracking reaction zone 110 at a weight hourly space velocity (WHSV) of from 3 per hour ($h^{-1}$) to 10,000 $h^{-1}$, such as from 3 $h^{-1}$ to 5000 $h^{-1}$, from 3 $h^{-1}$ to 2500 $h^{-1}$, from 3 $h^{-1}$ to 1000 $h^{-1}$, from 3 $h^{-1}$ to 100 $h^{-1}$, from 3 $h^{-1}$ to 12 $h^{-1}$, from 100 $h^{-1}$ to 5000 $h^{-1}$, or from 300 $h^{-1}$ to 2500 $h^{-1}$.

The cracking catalyst 112 may be activated by passing a flow of nitrogen gas through the cracking catalyst 112 at elevated temperature prior to contacting the feed stream 102 with the cracking catalyst 112 in the cracking reaction zone 110. In embodiments, the processes of the present disclosure can include, before contacting the feed stream 102 with the cracking catalyst 112, activating the cracking catalyst 112 with a flow of nitrogen gas at a temperature of from 450° C. to 650° C., or about 550° C. for a period of from 8 hours to 24 hours.

The butene-containing stream may be reacted by contact with the boronated zeolite catalyst in the cracking reaction zone, which can cause at least a portion of the butene-containing stream to undergo one or more catalytic cracking reactions to form one or more cracking reaction products, which may include ethylene, propylene, or both. The boronated zeolite catalyst, which may have a temperature equal to or greater than the reaction temperature of the cracking reaction zone, may transfer heat to the butene-containing stream to promote the endothermic cracking reaction.

The boronated zeolite catalyst may be operable to crack at least a portion of the butene-containing stream to produce a greater amount of light olefins, such as ethylene and propylene, in comparison to a zeolite without boron. Without intending to be bound by any particular theory, it is believed that the inclusion of boron in the zeolite catalyst can reduce aromatization activity, which can improve the yield of light olefins. Further, the method of forming the boronated ZSM-5 zeolite catalyst described herein can reduce the number of drying and calcining steps required to prepare the catalyst in comparison to boronated ZSM-5 zeolite catalysts formed by conventional methods, which can reduce the economic cost of forming the catalyst.

EXAMPLES

The various aspects of the present disclosure will be further clarified by the following examples. The examples are illustrative in nature and should not be understood to limit the subject matter of the present disclosure. In the Examples, boronated ZSM-5 zeolite catalysts according to the present disclosure were prepared. The materials used in preparing the boronated ZSM-5 zeolite catalysts of the Examples are provided below in Table 1.

TABLE 1

| Chemical | Supplier |
| --- | --- |
| Boric acid (≥99%) | Sigma Aldrich |
| Oxalic acid dehydrate (≥99%) | Sigma Aldrich |
| Citric acid anyhydrous (≥99%) | Alfa Aesar |
| ZSM-5 zeolite (CBV-2804) | Zeolyst International |
| Ammonium hydroxide (28-30% $NH_3$) | Sigma Aldrich |

Example 1: Preparation of Boronated ZSM-5 Zeolite Catalysts Using Oxalic Acid

To prepare the boronated ZSM-5 zeolite catalyst of Example 1, 4.528 grams (g) of boric acid and 4 g of oxalic acid dihydrate were dissolved in 200 mL of deionized water. 30 g of ZSM-5 zeolite (commercially available as CBV-2804 from Zeolyst International) having a silica-to-alumina ratio of 280 was added to the solution to form an initial slurry. The initial slurry was stirred gently at 80° C. for 24 hours to hydrothermally treat the initial slurry, producing a hydrothermally treated slurry that includes dealuminated ZSM-5 zeolite particles. The hydrothermally treated slurry was allowed to cool to room temperature. After cooling, the pH of the hydrothermally treated slurry was adjusted and monitored by adding a concentrated ammonium hydroxide solution (28-30% $NH_3$) until a desired value of a pH of 8-9 was obtained to produce a basic slurry. The basic slurry was stirred gently at 80° C. for 24 hours to hydrothermally treat the basic slurry and produce a boronated ZSM-5 zeolite slurry. The zeolite was filtered from the boronated ZSM-5 zeolite slurry and washed with deionized water until the pH of the filtrate reached 7. The resulting zeolite was dried on the oven at 90° C. overnight to produce a solid powder. The solid powder was calcined in air at 600° C. for 4 hours at rate of 2° C./min to produce the boronated ZSM-5 zeolite catalyst of Example 1.

Example 2: Preparation of Boronated ZSM-5 Zeolite Catalysts Using Citric Acid

The boronated ZSM-5 zeolite catalyst of Example 2 was prepared according to the procedure of Example 1 using citric acid anhydrous instead of oxalic acid dehydrate. Specifically, Example 2 was prepared using 4 g of citric acid anhydrous and did not include oxalic acid dihydrate to produce the boronated ZSM-5 zeolite catalyst of Example 2.

Example 3: Preparation of Boronated ZSM-5 Zeolite Catalysts Using Citric Acid and a Reduced Amount of Boric Acid The boronated ZSM-5 zeolite catalyst of Example 3 was prepared according to the procedure of Example 2, but the amount of boric acid used was reduced to 1 g to produce the boronated ZSM-5 zeolite catalyst of Example 3.

Comparative Example 4: Parent ZSM-5 Zeolite Catalyst

The ZSM-5 zeolite of Comparative Example 4 was the parent ZSM-5 zeolite (CBV-2804) used in Examples 1-3 without additional processing.

Example 5: Characterization of Boronated ZSM-5 Zeolite Catalysts

In Example 5, crystallinity and surface area, and microporous pore volume of the cracking catalysts of Examples 1-3 and Comparative Example 4 were evaluated. The crystallographic structures of the catalysts were obtained using X-ray diffraction (XRD). The relative crystallinity of Examples 1-3 in relation to the crystallinity of the initial zeolite material from which Examples 1-3 were formed was calculated based on the following equation: $X(\%)=100\%\times\Sigma A/\Sigma A_0$, where A is the sum of the five peak total area for each of Examples 1-3; and $A_0$ is the sum of the five peak total area of the reference sample (Comparative Example 4). The percent crystallinity of the catalysts of Examples 1-3 with respect to the parent zeolite (Comparative Example 4) is reported in Table 2. As shown by the crystallinity data in Table 2, the boronated zeolites of Examples 1-3 have similar crystallinity compared to the parent zeolite (Comparative Example 4). Surface area, pore volume, average pore size, and pore size distribution may be measured by $N_2$ adsorption isotherms performed at 77 Kelvin (K) (such as with a Micrometrics ASAP 2020 system). As would be understood by those skilled in the art, Brunauer, Emmett, and Teller (BET) analysis methods may be utilized to calculate the surface area, and the Barrett, Joyner and Halenda (BJH) calculation may be used to determine pore volume and pore size distribution. The surface area and microporous pore volume of the catalysts of Examples 1-3 and Comparative Example 4 are shown in Table 2. As shown in Table 2, the catalysts of Examples 1-3 demonstrated greater surface area and microporous more volume relative to the catalyst of Comparative Example 4.

TABLE 2

| Catalyst | % Crystallinity | Surface Area (m²/g) | Microporous pore volume (cc/g) |
| --- | --- | --- | --- |
| Example 1 | 96.6 | 530 | 0.155 |
| Example 2 | 95.3 | 550 | 0.160 |
| Example 3 | 93.7 | 545 | 0.158 |
| Comparative Example 4 | 100 | 477 | 0.140 |

Example 6: Boron NMR Characterization of Boronated ZSM-5 Zeolite Catalysts

In Example 6, the positions of the boron in the boronated ZSM-5 zeolite catalysts of Examples 1-3 were evaluated by measuring $^{11}B$ magic angle spinning (MAS) nuclear magnetic resonance (NMR) on a Varian 500 MHz nuclear magnetic resonance spectrometer, equipped with a 4 mm solids HX probe. To obtain $^{11}B$ MAS NMR spectra were obtained using a one pulse experiment, a relaxation delay of 3 seconds and a spinning frequency of 13 kHz. The $^{11}B$ chemical shifts were referenced externally to 0.1 M aqueous solution of $H_3BO_3$ (19.6 ppm). The peak characterizations from $^{11}B$ MAS NMR are shown in Table 3.

TABLE 3

| Catalyst | $^{11}B$ MAS NMR peak 1 (tetrahedral framework) shift (ppm) | $^{11}B$ MAS NMR peak 2 (trigonal planar framework) shift (ppm) | $^{11}B$ MAS NMR peak 3 (trigonal planar framework) shift (ppm) | $^{11}B$ MAS NMR peak 4 (trigonal planar extra-framework) shift (ppm) |
| --- | --- | --- | --- | --- |
| Example 1 | −3.01 | 0.74 | 7.04 | 17.45 |
| Example 2 | −2.97 | 0.78 | 6.82 | 17.24 |
| Example 3 | −2.94 | 0.65 | 7.04 | 17.34 |

As can be seen in Table 3, the Examples 1-3 have a first peak of about −3.0 attributed to boron being deposited in the tetrahedral framework position of the ZSM-5 zeolite catalyst. The examples have a second peak of about 0.70 and a third peak of about 7.0, both of which are attributed to boron being deposited within the trigonal planar framework position of the ZSM-5 zeolite catalyst. Further, Examples 1-3 have a fourth peak of about 17.0 attributed to boron being deposited within the trigonal planar extra-framework position of the ZSM-5 zeolite catalyst.

Example 7: Catalytic Evaluation of Boronated ZSM-5 Zeolite Catalysts

In Example 7, the cracking catalysts of Examples 1-3 and Comparative Example 4 were evaluated by conducting catalyst performance tests using a high-throughput screen reactor system manufactured by the HTE Company. The screen reactor system included 4 individual reactors that are grouped together and isothermally heated so that all the cracking catalysts are tested at the same reaction temperature of 550° C. The cracking catalysts were pressed and then sieved to a particle size of from 210 micrometers to 300 micrometers.

Referring now to FIG. 2, one reactor 300 of the screen reactor system for conducting the cracking catalyst evaluation is schematically depicted. Each reactor 300 includes a reaction chamber 302 having an inlet 304 and an outlet 306. The cracking catalyst 310 is placed in the reaction chamber 302 between two layers of silicon carbide 320. For a weight hourly space velocity of 7, the amount of cracking catalyst 310 for each evaluation was 0.14 grams. The reactor temperature was monitored by thermocouple 330 placed at three difference locations to ensure isothermal heating across the reactors 300.

To conduct the evaluation, the reactor was heated to a temperature of 120° C. and maintained at that temperature under a flow of nitrogen and argon for a period of 24 hours to ensure slow moisture desorption from the catalysts. The flowrate of argon was 6 mL/min and the flowrate of the nitrogen was 120 mL/min. The inlet and outlet were monitored to ensure no gas leakage from the system.

The cracking catalysts were then activated under a nitrogen flow of 120 mL/min, a temperature of 550° C., and for an activation period of 24 hours. Then, the nitrogen was turned off and a feed stream comprising mixed butenes was fed to the reactor for a period of a few days. The composition of the feed stream comprising mixed butenes is provided in Table 4. The same feed stream was used for all 4 cracking catalysts. The flow rate of the feed stream to each reactor of the screen reactor system was 0.267 grams per minute (g/min).

TABLE 4

| Component | Wt. % |
|---|---|
| 1-Butene | 45 |
| Cis-2-butene | 12.5 |
| Trans-2-butene | 12.5 |
| Iso-butane | 20 |
| n-butane | 10 |

Figure 3:
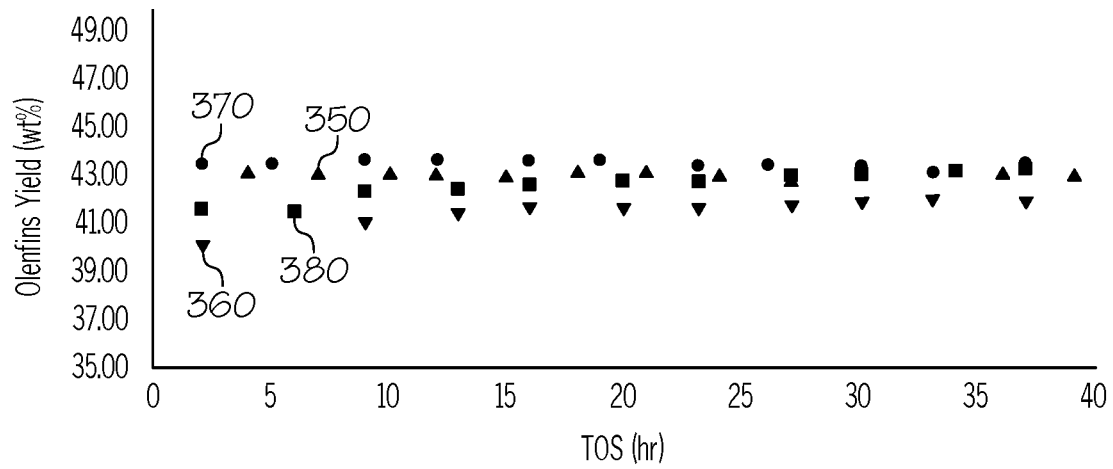
FIG. 3 graphically depicts light olefins yield (y-axis) versus time on stream (x-axis) for catalytic cracking of a butene-containing stream using catalysts of the examples, according to one or more embodiments described in the present disclosure.
Figure 4:
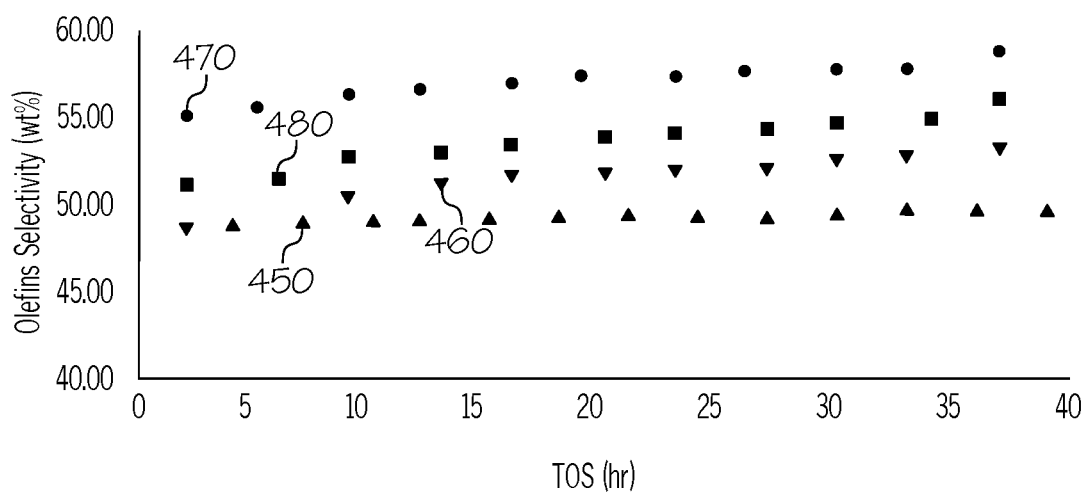
FIG. 4 graphically depicts light olefins selectivity (y-axis) versus time on-stream (x-axis) for catalytic cracking of a butene-containing stream using catalysts of the Examples, according to one or more embodiments described in the present disclosure.

An Agilent 7890B online gas chromatograph with helium as a carrier gas was used to analyze the products with a thermal conductivity detector (TCD) for light gases and two flame ionization detectors (FID) to identify C1-C6 hydrocarbons. The total olefins yield was determined from the measured compositions. In Example 7, the light olefins yield refers to the yield of propylene and ethylene. The light olefins yield does not include the amount of unreacted butenes. The results from the cracking of the butene-containing stream over the cracking catalysts of Examples 1-3 and Comparative Example 4 over time are shown in FIG. 3, which shows the light olefins yield of Comparative Example 4 (ref. no. 350), Example 1 (ref. no. 360), Example 2 (ref no. 370), and Example 3 (ref no. 380), and FIG. 4, which shows the light olefins selectivity of Comparative Example 4 (ref no. 450), Example 1 (ref. no. 460), Example 2 (ref. no. 470), and Example 3 (ref. no. 480). The average light olefins yield, average light olefins selectivity, and average percent improvement of light olefins selectivity for each of the cracking catalysts of Examples 1-3 and Comparative Example 4 are provided in Table 5. As can be seen in Table 5, the average light olefins selectivity using the cracking catalysts of Examples 1-3 was greater than the parent ZSM-5 zeolite (Comparative Example 4).

TABLE 5

| Material | Average Light Olefins Yield (wt. %) | Average Light Olefins Selectivity (wt. %) | Average % Improvement (Light Olefins Selectivity) |
|---|---|---|---|
| Example 1 | 43.5 | 57.4 | 15.7 |
| Example 2 | 41.3 | 51.3 | 3.4 |
| Example 3 | 42.8 | 54.0 | 8.9 |
| Comparative Example 4 | 43.0 | 49.6 | — |

A first aspect of the present disclosure is directed to a method of making a boronated zeolite catalyst, the method comprising preparing an initial slurry comprising water, a shape selective zeolite, boric acid, and a weak acid selected from the group consisting of oxalic acid, citric acid, and oxalic acid and citric acid, where the initial slurry may have an initial pH of from 1 to 5, hydrothermally treating the initial slurry at a temperature of from 70° C. to 90° C. to produce a hydrothermally treated slurry comprising dealuminated zeolite particles, adjusting the pH of the hydrothermally treated slurry to an intermediate pH of from 8 to 9 to produce a basic slurry, after adjusting the pH to the intermediate pH, hydrothermally treating the basic slurry at a temperature of from 70° C. to 90° C. to produce a boronated zeolite slurry, removing liquids from the boronated zeolite slurry to produce a boronated zeolite filtrate, and drying and calcining the boronated zeolite filtrate to produce the boronated zeolite catalyst.

A second aspect of the present disclosure may include the first aspect, where hydrothermally treating the initial slurry may comprise stirring the slurry and heating the slurry for a time of from 12 hours to 36 hours.

A third aspect of the present disclosure may include either one of the first or second aspects, where hydrothermally treating the initial slurry may remove at least a portion of aluminum from the shape selective zeolite.

A fourth aspect of the present disclosure may include any one of the first through third aspects, where the hydrothermally treated slurry is not actively dried or calcined before adjusting the pH to the intermediate pH.

A fifth aspect of the present disclosure may include any one of the first through fourth aspects, further comprising, after hydrothermally treating the initial slurry, allowing the hydrothermally treated slurry to return to room temperature.

A sixth aspect of the present disclosure may include any one of the first through fifth aspects, where adjusting the pH of the hydrothermally treated slurry may comprise adding ammonium hydroxide to the hydrothermally treated slurry and monitoring the pH of the hydrothermally treated slurry until the pH is from 8 to 9.

A seventh aspect of the present disclosure may include any one of the first through sixth aspects, where hydrothermally treating the basic slurry may comprise stirring the basic slurry and heating the basic slurry for a time of from 12 to 36 hours.

An eighth aspect of the present disclosure may include any one of the first through seventh aspects, where the boronated zeolite filtrate may be washed before the drying and calcining.

A ninth aspect of the present disclosure may include any one of the first through eighth aspects, where calcining the solid powder may comprise heating the solid powder to a temperature of from 500° C. to 700° C.

A tenth aspect of the present disclosure may include any one of the first through ninth aspects, where the shape selective zeolite of the initial slurry may have an average silica to alumina molar ratio of from 15 to 800.

An eleventh aspect of the present disclosure may include any one of the first through tenth aspects, where the initial slurry may comprise from 5 weight percent to 20 weight percent of the shape selective zeolite, based on the total weight of the initial slurry.

A twelfth aspect of the present disclosure may include any one of the first through eleventh aspects, where the shape selective zeolite may be ZSM-5 zeolite.

A thirteenth aspect of the present disclosure may include any one of the first through twelfth aspects, where the initial slurry may comprise from 0.01 weight percent to 1 weight percent of the boric acid, based on the total weight of the initial slurry.

A fourteenth aspect of the present disclosure may include any one of the first through thirteenth aspects, where the initial slurry may comprise from 0.01 weight percent to 1 weight percent of the weak acid, based on the total weight of the initial slurry.

A fifteenth aspect of the present disclosure may include any one of the first through fourteenth aspects, where the method does not include steaming to dealuminate the shape selective zeolite.

A sixteenth aspect of the present disclosure may include a boronated zeolite catalyst made by the method of any one of the first through fifteenth aspects, where boron may be disposed at tetrahedral and trigonal planar sites within a framework of the boronated zeolite catalyst, and boron may disposed on the zeolite in trigonal planar extra-framework sites of the boronated zeolite catalyst.

A seventeenth aspect of the present disclosure may include the sixteenth aspect, where the boronated zeolite catalyst may comprise from 3 weight percent to 15 weight percent boron, based on the total weight of the boronated zeolite catalyst.

An eighteenth aspect of the present disclosure may include any one of the sixteenth or seventeenth aspects, where the boronated zeolite catalyst may have a silica to alumina molar ratio of from 20 to 1600.

A nineteenth aspect of the present disclosure may include any one of the sixteenth through eighteenth aspects, where the boronated zeolite catalyst may have an average surface area of greater than or equal to 500 m$^2$/g.

A twentieth aspect of the present disclosure may include any one of the sixteenth through nineteenth aspects, where the boronated zeolite catalyst may have an average microporous pore volume of greater than or equal to 0.15 centimeters cubed per gram.

A twenty-first aspect of the present disclosure may be directed to a process for cracking a butene-containing stream, the process comprising contacting the butene-containing stream with the boronated zeolite catalyst of any one of the sixteenth through twentieth aspects in a reactor, where contacting may cause at least a portion of butene to undergo cracking reactions to form a product stream comprising ethylene and propylene.

A twenty-second aspect of the present disclosure may include the twenty-first aspect, where the butene-containing stream may comprise greater than or equal to 40 wt. % mixed butenes based on the total weight of the butene-containing stream.

A twenty-third aspect of the present disclosure may include either the twenty-first or twenty second aspect, where the butene-containing stream may comprise 40 wt. % to 50 wt. % 1-butene, 10 wt. % to 20 wt. % cis-2-butene, 10 wt. % to 20 wt. % trans-2-butene, and 15 wt. % to 30 wt. % isobutane, based on the total weight of the butene-containing stream.

A twenty-fourth aspect of the present disclosure may include any one of the twenty-first through twenty-third aspects, where a temperature of the reactor during the contacting may be from 300° C. to 650° C.

It is noted that any two quantitative values assigned to a property may constitute a range of that property, and all combinations of ranges formed from all stated quantitative values of a given property are contemplated in this disclosure.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific aspects, it is noted that the various details of such aspects should not be taken to imply that these details are essential components of the aspects. Rather, the claims appended hereto should be taken as the sole representation of the breadth of the present disclosure and the corresponding scope of the various aspects described in this disclosure. Further, it will be apparent that modifications and variations are possible without departing from the scope of the appended claims.

What is claimed is:

1. A method of making a boronated zeolite catalyst, the method comprising:
    preparing an initial slurry comprising water, a shape selective zeolite, boric acid, and a weak acid selected from the group consisting of oxalic acid, citric acid, and oxalic acid and citric acid, where the initial slurry has an initial pH of from 1 to 5;
    hydrothermally treating the initial slurry at a temperature of from 70° C. to 90° C. to produce a hydrothermally treated slurry comprising dealuminated zeolite particles;
    adjusting the pH of the hydrothermally treated slurry to an intermediate pH of from 8 to 9 to produce a basic slurry;
    after adjusting the pH to the intermediate pH, hydrothermally treating the basic slurry at a temperature of from 70° C. to 90° C. to produce a boronated zeolite slurry;
    removing liquids from the boronated zeolite slurry to produce a boronated zeolite filtrate; and
    drying and calcining the boronated zeolite filtrate to produce the boronated zeolite catalyst.

2. The method of claim 1, where hydrothermally treating the initial slurry comprises stirring the slurry and heating the slurry for a time of from 12 hours to 36 hours.

3. The method of claim 1, where hydrothermally treating the initial slurry removes at least a portion of aluminum from the shape selective zeolite.

4. The method of claim 1, where the hydrothermally treated slurry is not actively dried or calcined before adjusting the pH to the intermediate pH.

5. The method of claim 1, further comprising, after hydrothermally treating the initial slurry, allowing the hydrothermally treated slurry to return to room temperature.

6. The method of claim 1, where adjusting the pH of the hydrothermally treated slurry comprises adding ammonium hydroxide to the hydrothermally treated slurry and monitoring the pH of the hydrothermally treated slurry until the pH is from 8 to 9.

7. The method of claim 1, where hydrothermally treating the basic slurry comprises stirring the basic slurry and heating the basic slurry for a time of from 12 to 36 hours.

8. The method of claim 1, where the boronated zeolite filtrate is washed before the drying and calcining.

9. The method of claim 1, where calcining the boronated zeolite filtrate comprises heating the boronated zeolite filtrate to a temperature of from 500° C. to 700° C.

10. The method of claim 1, where the shape selective zeolite of the initial slurry has an average silica to alumina molar ratio of from 15 to 800.

11. The method of claim 1, where the shape selective zeolite is ZSM-5 zeolite.

12. The method of claim 1, where the initial slurry comprises:
    from 5 weight percent to 20 weight percent of the shape selective zeolite;
    from 0.01 weight percent to 1 weight percent of the boric acid;
    from 0.01 weight percent to 1 weight percent of the weak acid, based on the total weight of the initial slurry; or combinations of these constituents.

* * * * *